United States Patent [19]

Young

[11] Patent Number: 4,892,960

[45] Date of Patent: Jan. 9, 1990

[54] CRYSTALLINE LYSOCELLIN COMPOSITIONS AND METHOD OF MAKING

[75] Inventor: Vernon V. Young, Terre Haute, Ind.

[73] Assignee: International Minerals & Chemical Corp., Northbrook, Ill.

[21] Appl. No.: 810,910

[22] Filed: Dec. 20, 1985

Related U.S. Application Data

[63] Continuation of Ser. No. 695,419, Jan. 28, 1985, abandoned, which is a continuation of Ser. No. 291,133, Aug. 7, 1981, abandoned.

[51] Int. Cl.$^4$ .......................................... C07D 309/10
[52] U.S. Cl. .................................................. 549/414
[58] Field of Search ........................................ 549/414

[56] References Cited

U.S. PATENT DOCUMENTS

| | | | |
|---|---|---|---|
| 3,794,732 | 5/1974 | Raun | 424/283 |
| 4,033,823 | 7/1977 | Liu et al. | 195/80 |
| 4,305,956 | 12/1981 | Shibuya et al. | 549/414 |

OTHER PUBLICATIONS

Westley, J. W.: Polyether Antibiotics: Versatile Carboxylic Acid Ionophores Produced by Streptomyces, Advances in Applied Microbiology 22:177–223, 1977.
Ebata, E., et al: Lysocellin, A New Polyether Antibiotic, Journal of Antibiotics 28(2):118–121, 1975.
Otake, N., et al: The Assignment of the $^{13}$C—NMR Spectrum of Lysocillin and Its Biosynthesis, Agric. Biol. Chem. 42(10):1879–1886, 1978.
N. Otake et al., J.C.S. Chem. Comm., 1975, pp. 92–93.
J. W. Westley, Advances in Applied Microbiology, 22:177–223 (1977).
Martin et al., Chem. Abstract, 94, 137 806c (1981) (Abstract of Ger. Offen. 3,026,408).
Martin et al., Chem. Abstract, 95, 103,314w (1981) (Abstract of Brit. Pat. 2,055,094).

*Primary Examiner*—Nicky Chan
*Attorney, Agent, or Firm*—George R. Repper; Thomas L. Farquer

[57] ABSTRACT

Crystalline lysocellin compositions, and method of making them. These compounds are useful for promoting growth and feed efficiency in food producing mammals by administering growth promoting amounts of the compounds to such mammals. In particular, the crystalline free acid and the crystalline zinc, copper and manganese of lysocellin can be made according to the disclosed methods.

5 Claims, No Drawings

CRYSTALLINE LYSOCELLIN COMPOSITIONS AND METHOD OF MAKING

This is a continuation of application Ser. No. 695,419 filed Jan. 28, 1985 now abandoned, which is a continuation of application Ser. No. 291,133 filed Aug. 7, 1981 now abandoned.

BACKGROUND OF THE INVENTION

The present invention relates to crystalline lysocellin compositions, and methods of making them, in particular the crystalline free acid and the crystalline zinc, copper and manganese salts of lysocellin are disclosed. The subject compositions are useful as growth-promoting substances in food-producing animals.

A fairly comprehensive review of the various classes of polyether antibiotics is set forth in Westley, *Adv. Appl. Microbiology* 22, 177–223 (1977). Lysocellin falls into Class 2a as defined by Westley.

Lysocellin was first reported in the literature by Ebata, et al, *The Journal of Antibiotics* 28(2):118–121, 1975. The physico-chemical properties of lysocellin are described there, including a melting point of about 158°–160° C. of the colorless needles of the sodium salt, but there is no disclosure here of a stable, crystalline free acid form of lysocellin. The antibiotic is said to be produced from a mutant strain of *Streptomyces cacaoi* var. *asoensis* designated *Streptomyces cacaoi* var. *asoensis* K-9 Met-. This reference discloses that lysocellin is active against grampositive bacteria, antibiotic resistant *Staphylococcus aureus,* some fungi, but that it is not active against gramnegative bacteria.

The structural formula for lysocellin was set forth by Otake, et al, *Agric. Biol. Chem.* 42(10):1879–1887, 1978. The crystalline silver salt and the crystalline sodium salt of lysocellin are disclosed, but there is no disclosure of the method for obtaining these. In addition, there is no disclosure here of a crystalline, free acid form of lysocellin or of zinc manganese or copper lysocellin in crystalline form.

U.S. Pat. No. 4,033,823 issued July 3, 1977, to Liu, et al, discloses the structural formula of lysocellin and a method for making it using *Streptomyces longwoodensis* (ATCC 29251). This patent describes only the use of lysocellin as an antimicrobial.

In a commonly assigned copending application filed on even date herewith, it is reported that the various forms of lysocellin act as especially effective growth-promoting and feed efficiency-enhancing agent when administered to food-producing mammals such as ruminants. In ruminants having a developed rumen function, including cattle, sheep and goats, the various forms of lysocellin are believed to promote growth and enhance the efficiency of feed utilization in the animal by lowering the acetate/propionate ratio among the volatile fatty acids (VFA) found in the animal's rumen fluid. The relationship between acetate/propionate ratio in the rumen and feed efficiency in the ruminant animals is explained in greater detail in Raun, U.S. Pat. No. 3,794,732 issued Feb. 26, 1974.

The present invention is directed to the crystalline free acid and zinc, manganese and copper salt forms of lysocellin and to a novel method of obtaining these crystalline compositions. As mentioned, these compositions are useful for promoting growth and enhancing feeding efficiency in food-producing mammals, to meat-producing animals, particularly ruminants.

Lysocellin-containing fermentation broth is prepared in conventional manner by fermenting a nutrient-containing liquid fermentation medium inoculated with a *Streptomyces lonqwoodensis* (ATCC 29251) which is capable of producing lysocellin. Suitable liquid fermentation media are generally aqueous dispersions containing a nitrogen source and a carbohydrate source. Nitrogen sources for use in the fermentation media herein can include, for example, sugar, molasses, corn-steep liquor and the like. The fermentation media can also contain a variety of optional ingredients, if desired, such as for example, pH adjustment agents, buffers, trace minerals, antifoam agents, filter aids, etc.

The Streptomyces microorganism is grown in an aerated, agitated, submerged culture with the pH of the broth adjusted to about neutral, i.e., from a pH value of about 6.5 to about 7.5. Fermentation can generally be carried out at slightly elevated temperatures, e.g., between about 25° C. and 35° C. Incubation of the broth can be carried out for a period of several days, e.g., from about 4 to 6 days or longer if it is economically advantageous to do so.

A particular method for producing the antibiotic lysocellin was disclosed by Liu et al in U.S. Pat. No. 4,033,823 by the cultivation of a strain of *Streptomyces longwoodensis* which is on unrestricted deposit at the American Type Culture Collection under the designation ATCC 29251. The structure of lysocellin is as follows:

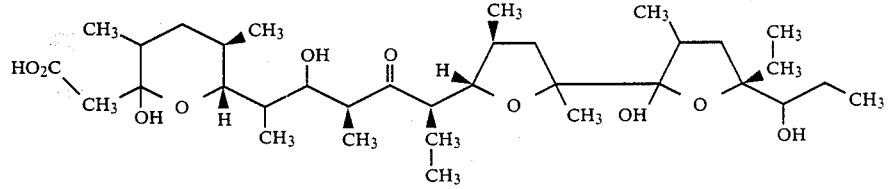

Methods for preparing the lysocellin antibiotic are set forth in the above-mentioned patent. The characteristics of lysocellin were first set forth in the article by Ebata et al, *J. Antibiotics* 28:118–121, 1975.

The various forms of lysocellin, including the free acid, sodium salts, and the zinc, manganese and copper lysocellin in complexes used in the present invention act as growthpromoting agents in food-producing mammals, e.g., ruminants and swine. These forms of lysocellin can be administered to food-producing mammals, either orally, subcutaneously, or parenterally, in amounts sufficient to enhance the growth rate of the animal. The amount of the lysocellin material administered to an animal varies, of course, with the species of animal, the desired rate of growth, and the like. The material is frequently administered to ruminants in an amount of about 1 to 200, preferably about 1 to 50 milligrams per head per day.

The various lysocellin materials, their preparation and recovery and the feed and feed additive compositions involved in the present invention as well as their usefulness as growth promoting agents for ruminants are illustrated by the following examples. Such examples include the preparation, recovery and evaluation of the preferred lysocellin material, but are in no way limiting of the present invention to processes involving that particular material.

EXAMPLE I

Crystalline sodium lysocellin was produced following the fermentation method set forth in Example 1 of U.S. Pat. No. 4,033,823 issued July 5, 1977, which procedure is incorporated herein by reference. The melting point of the resultant crystalline sodium lysocellin isolated from the fermentation broth was 159.6° C. (Mettler). Infra-red spectrum and optical rotation agree with the data for sodium lysocellin published by Otake, et al op. cit. NMR spectra and elemental analysis of the crystalline material obtained by the above method confirmed that the product was sodium lysocellin.

EXAMPLE II

Sodium lysocellin produced by the method of Example I was used to make the free acid of lysocellin as follows:

3.9 g sodium lysocellin @ (0.006 moles) and 1.4 g zinc acetate hydrate $[Zn(Ac)_2.2H_2O]$@ (0.006 mole) were mixed together in 30 ml denatured ethanol (3A). The sodium lysocellin was first suspended in the ethanol and stirred, and the zinc acetate hydrate was added, and the suspension stirred at room temperature until everything was dissolved. The pH was then adjusted to a range of 2-4 with 37% HCl. Stirring was continued for 20-30 minutes until precipitation of a birefringent material started. Precipitation was continued by adding water dropwise (holding pH at 4) until about 60 ml of water was added. The resulting crystalline precipitate of the free acid of lysocellin was isolated and dried. Th resulting free acid of lysocellin comprises birefringent crystals.

The above material was again dissolved in ethanol and recrystallized from ethanol by again adding water dropwise until the free acid of lysocellin precipitated out as birefringent crystals. The melting point of this material was about 147.5° C. (Mettler), and the analysis (percent by weight) was about: C, 65.49%; H, 9.57%; and 0, 24.90% and showed the molecule to comprise $C_{34}H_{60}O_{10}$ (lysocellin, free acid).

EXAMPLE III

The sodium lysocellin made according to the method of Example I was used to make the crystalline zinc salt of lysocellin by the following method:

1.3 g of sodium lysocellin and 0.5 g of zinc acetate hydrate $[Zn(Ac)_2.2 H_2O]$ were added to 15 ml of acetone. The reactants were stirred at room temperature until all solids were in solution. Stirring was continued, and 30 ml of water was added dropwise to cause precipitation of the zinc salt complex of lysocellin. The crystalline precipitate was isolated and dried, redissolved in acetone and then recrystallized using the above procedure to yield the crystalline zinc lysoellin salt complex. The melting point of this material was about 109.5° C. (Mettler). The analysis was about: C, 59.77%; H, 8.94%; 0, 23.65%; Zn, 4.37%, indicating that two molecules of lysocellin are tied up with one zinc cation in the zinc salt complex as follows: $(C_{34}H_{59}O_{10})_2Zn$. It is contemplated that other salts of zinc can be used instead of zinc acetate, including zinc chloride, zinc sulfate and zinc nitrate.

EXAMPLE IV

Example III was repeated, except that zinc acetate hydrate was replaced by manganese acetate hydrate. The resulting manganese salt complex of lysocellin had an analysis of 3.73% Mn, indicating that two molecules of lysocellin are tied up by one bivalent manganese cation as follows: $(C_{34}H_{59}O_{10})_2Mn$. It is contemplated that other salts of manganese can be used in this procedure, including the chloride, sulfate and nitrate salts.

EXAMPLE V

The method of Example III was repeated, except that the zinc acetate hydrate was replaced by cupric acetate hydrate $[Cu(Ac)_2.2H_2O]$. A mixture of 2.6 g of sodium lysocellin, 1.0 g cupric acetate hydrate and 50 ml of acetone was stirred until solution was complete. Stirring was continued, and water (2 vol) was added dropwise. The copper salt complex of lysocellin was precipitated, isolated and recrystallized from aqueous acetone. The crystalline copper salt complex of lysocellin had a melting point of 119°-122° C. and it had an analysis of 3.68% by weight copper, indicating there are two molecules of lysocellin tied up by one bivalent copper cation as follows: $(C_{34}H_{59}O_{10})_2Cu$. It is contemplated that other salts of copper can be used instead of the acetate salt, including the chloride, sulfate and nitrate salts.

EXAMPLE VI

The in vitro rumen fermentation test described below can be used to accurately predict the improved feed utilization effects of test compounds fed to ruminants.

Microorganisms in the rumen of the animal ferment carbohydrates to produce monosaccharides and then degrade the monosaccharides to pyruvate compounds. Pyruvate is then metabolized by microbiological processes to either acetate or proprionate compounds. These compounds may be either acids or other forms of the radicals. Two acetate compounds may be combined still in the rumen to form butyrates.

The animal can utilize butyrate, propionate and acetate with differing degrees of efficiency. Butyrate is utilized most efficiently and acetate the least efficiently. The relative efficiency of butyrate is negated because it is made from acetate in the rumen.

One of the major inefficiencies in the rumen is in the manufacture of acetate. Since it is made by the degradation of a pyruvate molecule, each molecule of acetate produced is accompanied by molecule of methane. Most of the methane produced is lost through eructation. Each molecule of butyrate used involves the loss of two molecules of methane with all its associated energy.

Thus the efficiency of carbohydrate utilization (carbohydrates being the major nutritive portion of animals'feed) can be increased by treatments which encourage the animal to produce propionate rather than acetate from the carbohydrates.

The efficiency of feed use can be effectively monitored by observing the production and concentration of propionate compounds in the rumen. If the animal is making more propionate, it will be found to be using its feed more efficiently. This efficiency is manifested by greater weight gains per feed intake, a reduction in energy losses by methane release, and economic advantages to the animal grower when the animal is sold for consumption.

Procedure

Rumen fluid was removed from a fistulated steer and strained through cheesecloth. An equal amount of pH 7 buffer was added to the strained rumen fluid. After layering occurred, the lower layer was saved and again diluted with an equal amount of buffer.

Ten ml aliquotes of the buffered rumen fluid were added to fermentation vessels containing 500 mg of fresh finely ground cattle ration, 1 mg of cellubiose, and amounts of the test compounds that resulted in a 5 ppm concentration.

The vessels were outfitted with one way gas valves and placed in a incubator shaker for 24 hours at 38° C. Fermentation was stopped by the addition of one ml of mercuric chloride.

The liquid was decanted and analysed for volatile fatty acid by gas chromatography.

Conclusions

Changes in the acetate/propionate ratio caused by six forms of the polyether antibiotic lysocellin were determined by the above in vitro methods. The acetate/propionate weight ratios given are from means of 10 tests for each compound.

| Negative Control | Positive Control Monensin | Example I Lysocellin Na | Example II Lysocellin Free Acid | Ex. III Lysocellin Zn | Example IV Lysocellin Mn | Example V Lysocellin Cu |
|---|---|---|---|---|---|---|
| 2.04 | 1.38 | 1.24 | 1.26 | 1.24 | 1.26 | 1.22 |

All forms of lysocellin tested were more effective than the positive control, monensin, in increasing the relative amount of propionate. From these results it can be concluded that all forms of lysocellin can be expected to improve feed efficiency when fed to ruminants. The fact that all forms of lysocellin performed substantially better than monensin would also indicate a possible effect as a growth promoter.

EXAMPLE VII

Twenty-five Columbia wether lambs were received and adapted to the basal ration set forth below in Table 1.

TABLE 1

Composition of the Basal Ration Wether Lamb Test

| | International Reference No. | Percent |
|---|---|---|
| Corn, cracked shelled | 4-20-931 | 68.7 |
| Alfalfa-whole corn plant, dehydrated[a] | | 20.0 |
| Soybean meal (44%) | 5-20-637 | 7.5 |
| Cane molasses | 4-04-696 | 2.0 |
| Limestone | 6-02-632 | 0.8 |
| Trace mineral salt[b] | | 0.6 |
| Vitamin premix[c] | | 0.4 |
| Calculated composition (as fed basis) | | |
| Crude protein | | 11.9 |
| Crude fiber | | 6.8 |
| Calcium | | 0.48 |
| Phosphorus | | 0.28 |
| Potassium | | 0.73 |
| Sulfur | | 0.27 |
| Digestible energy | | 3.08 Mcal/kg |

[a]Charles H. Schenk and Sons, Inc., Vincennes, Indiana. Guaranteed analysis: crude protein, min. 12.00%; crude fiber, max. 25.00%; fat, min. 1.50%; calcium, min. 0.75%, max 0.87%; and phosphorus, min. 0.20%.
[b]Composition: NaCl, not >99.0%; not <0.35% Zn, 0.34% Fe, 0.200% Mn, 0.033% Cu, 0.077% I, and 0.005% Co.
[c]Provides per kg of diet: 2750 IU vitamin A; 700 IU vitamin D, and 10 IU vitamin E.

Animals

Six days after arrival, the lambs were weighed, tagged, injected with Tramisol wormer and vaccinated for both contagious ecthyma (soremouth) and Clostridium perfringes type D (overeating disease). Following adaptation, the lambs were reweighed. The lambs were then randomly assigned to five pens (five lambs per pen), providing approximately 1.42 sq. m. per animal. During the following eight-week experimental period, water and feed were available ad libitum.

Compounds Tested

There were four lysocellin materials tested, and a negative control. The test diets and control were each administered to five animals over the eight week test period. Each test ration contained the designated lysocellin compound at a level of 30 g/ton.

Procedures

The lambs were weighed initially, and biweekly thereafter for the duration of the eight week experiment. The lambs were fasted for eighteen hours prior to weighing. Orts were weighed back at 3:00 P.M. the day prior to weighing the animals.

The effect of the dietary treatments is shown in Table 2 below:

TABLE 2

Effects of Addition to Ration of Various Lysocellin Materials in Wegher Lambs

| Effect Observed | Control | Sodium Lysocellin | Zinc Lysocellin | Lysocellin (Free Acid) | Manganese Lysocellin |
|---|---|---|---|---|---|
| Avg. Daily Gain (kg/day/head) | 0.206 | 0.198 | 0.204 | 0.198 | 0.235 |
| Gain/Feed | 0.148 | 0.157 | 0.155 | 0.153 | 0.171 |

Of the above treatments, manganese lysocellin was most effective in increasing gain (growth promotion) and feed efficiency. Each of the test compositions showed some improvement in feed efficiency weight ratio (gain/feed), and it is expected that when the dosage for each lysocellin material is optimized, all lysocellin materials will show an increase in gain (growth promotion) comparable, or better than, that observed for the manganese lysocellin material.

The subject invention provides additional novel forms of crystalline lysocellin and novel methods for obtaining them not disclosed in the references known to applicant. As pointed out above, the acid form of lysocellin is disclosed by Otake et al op. cit. as an amorphous powder.

The crystalline lysocellin salts of zinc and copper are not disclosed in any reference known to applicant, and the disclosed method for obtaining these crystalline salts is also believed to be novel. The crystalline forms of lysocellin provide handling advantages, increased levels of purity and dosage uniformity, as well as added stability.

What is claimed is:

1. A crystalline lysocellin composition selected from the group consisting of the crystalline free acid of lysocellin, crystalline zinc lysocellin, crystalline manganese lysocellin and crystalline copper lysocellin.

2. The crystalline free acid of lysocellin composition of claim 1 having a melting point of about 147.5° C. (Mettler) and a per cent by weight chemical analysis of about: C, 65.49%, H, 9.57%; and O, 24.90%.

3. The crystalline zinc lysocellin composition of claim 1 having a melting point of about 109.5° C. (Mettler) and a per cent by weight chemical analysis of about C, 59.77%; H, 8.94%, O, 23.65%; and Zn. 4.37%.

4. The crystalline manganese lysocellin composition of claim 1 having per cent by weight analysis of about 3.73% by weight manganese, and consisting of two molecules of lysocellin to one bivalent manganese cation.

5. The crystalline copper lysocellin composition of claim 1 having a per cent by weight analysis of about 3.68% by weight copper, and consisting of two molecules of lysocellin to one bivalent copper cation.

* * * * *